(12) United States Patent
Behnke et al.

(10) Patent No.: US 8,403,924 B2
(45) Date of Patent: *Mar. 26, 2013

(54) SHIELDING FOR AN ISOLATION APPARATUS USED IN A MICROWAVE GENERATOR

(75) Inventors: Robert J. Behnke, Erie, CO (US); Tom E. McMunigal, Mead, CO (US)

(73) Assignee: Vivant Medical, Inc., Boulder, CO (US)

( * ) Notice: Subject to any disclaimer, the term of this patent is extended or adjusted under 35 U.S.C. 154(b) by 1218 days.

This patent is subject to a terminal disclaimer.

(21) Appl. No.: 12/203,734

(22) Filed: Sep. 3, 2008

(65) Prior Publication Data

US 2010/0057076 A1    Mar. 4, 2010

(51) Int. Cl.
A61B 18/04    (2006.01)
(52) U.S. Cl. ............................ 606/34; 606/32
(58) Field of Classification Search ............. 606/32–34, 606/45–47; 330/313, 136
See application file for complete search history.

(56) References Cited

U.S. PATENT DOCUMENTS

| | | | |
|---|---|---|---|
| 3,908,176 A | 9/1975 | DeBoer et al. | |
| 4,229,714 A * | 10/1980 | Yu | 333/12 |
| 5,097,846 A | 3/1992 | Larsen | |
| 5,405,346 A | 4/1995 | Grundy et al. | |
| 5,562,720 A | 10/1996 | Stern et al. | |
| 5,683,382 A | 11/1997 | Lenihan et al. | |
| 5,693,082 A * | 12/1997 | Warner et al. | 607/156 |
| 5,865,788 A | 2/1999 | Edwards et al. | |
| 5,904,709 A | 5/1999 | Arndt et al. | |
| 5,931,836 A | 8/1999 | Hatta et al. | |
| 5,957,969 A | 9/1999 | Warner et al. | |
| 5,961,871 A | 10/1999 | Bible et al. | |
| 5,983,141 A | 11/1999 | Sluijter et al. | |
| 6,016,452 A | 1/2000 | Kasevich | |
| 6,067,475 A | 5/2000 | Graves et al. | |
| 6,097,985 A | 8/2000 | Kasevich et al. | |
| 6,134,476 A | 10/2000 | Arndt et al. | |
| 6,175,768 B1 | 1/2001 | Arndt et al. | |
| 6,181,970 B1 | 1/2001 | Kasevich | |
| 6,216,704 B1 | 4/2001 | Ingle et al. | |
| 6,233,490 B1 | 5/2001 | Kasevich | |
| 6,246,912 B1 | 6/2001 | Sluijter et al. | |
| 6,273,886 B1 | 8/2001 | Edwards et al. | |
| 6,358,245 B1 | 3/2002 | Edwards et al. | |

(Continued)

FOREIGN PATENT DOCUMENTS

| DE | 179607 | 3/1905 |
|---|---|---|
| DE | 1099658 | 2/1961 |

(Continued)

OTHER PUBLICATIONS

U.S. Appl. No. 12/057,557, filed Mar. 28, 2008.

(Continued)

*Primary Examiner* — Nicholas Lucchesi
*Assistant Examiner* — Leah Stohr

(57) ABSTRACT

A system for reducing radiated emissions the system including a microwave generator that supplies microwave energy at a fundamental frequency, a coaxial transmission cable that transmits microwave energy between the microwave generator and a microwave energy delivery device and an isolation apparatus connected between the microwave generator and the coaxial transmission cable. The isolation apparatus is configured to electrically isolate the coaxial transmission cable from the microwave generator and capacitively couple the microwave generator ground to the coaxial transmission cable.

9 Claims, 5 Drawing Sheets

U.S. PATENT DOCUMENTS

| | | |
|---|---|---|
| 6,471,696 B1 | 10/2002 | Berube et al. |
| 6,485,486 B1 | 11/2002 | Trembly et al. |
| 6,699,241 B2 | 3/2004 | Rappaport et al. |
| 6,743,225 B2 | 6/2004 | Sanchez et al. |
| 6,778,044 B2 | 8/2004 | Fehrenbach et al. |
| 6,784,405 B2 | 8/2004 | Flugstad et al. |
| 6,847,848 B2 | 1/2005 | Sterzer et al. |
| 7,200,010 B2 | 4/2007 | Broman et al. |
| 7,226,446 B1 | 6/2007 | Mody et al. |
| 7,344,533 B2 | 3/2008 | Pearson et al. |
| 7,393,352 B2 | 7/2008 | Berube |
| 7,419,487 B2 | 9/2008 | Johnson et al. |
| 2002/0087151 A1 | 7/2002 | Mody et al. |
| 2005/0033278 A1 | 2/2005 | McClurken et al. |
| 2006/0224152 A1 | 10/2006 | Behnke et al. |
| 2007/0203480 A1 | 8/2007 | Mody et al. |
| 2007/0233057 A1 | 10/2007 | Konishi |
| 2007/0282319 A1 | 12/2007 | Van Der Weide et al. |
| 2009/0018536 A1 | 1/2009 | Behnke |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 42 06 433 | 9/1993 |
| DE | 4339049 | 5/1995 |
| DE | 19717411 | 11/1998 |
| DE | 19848540 | 5/2000 |
| EP | 246350 | 11/1987 |
| EP | 0 267 403 | 5/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 0 882 955 | 12/1998 |
| EP | 1051948 | 11/2000 |
| EP | 1186274 | 4/2006 |
| EP | 880220 | 6/2006 |
| EP | 1810630 | 7/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO2006/105121 | 10/2006 |

OTHER PUBLICATIONS

U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized..." Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report EP09169377.0 dated Dec. 15, 2009.

* cited by examiner

SHIELDING FOR AN ISOLATION APPARATUS USED IN A MICROWAVE GENERATOR

BACKGROUND

1. Technical Field

The present disclosure relates to systems and methods for performing a medical procedure, wherein the medical procedure includes the generation and safe transfer of energy from an energy source to a microwave energy delivery device. More particularly, a microwave energy delivery system including an isolation apparatus is disclosed to reduce undesirable radiated emissions during the delivery of microwave energy.

2. Background of Related Art

Microwave delivery systems and ablation procedures using microwave energy are designed to safely deliver microwave energy to a target tissue. The equipment, the act of energy delivery or the procedures used to deliver energy may be regulated by various governmental or industrial regulations or standards, such as, for example, FCC regulations and standards for microwave equipment or electromagnetic compatibility (EMC) regulations and standards to ensure that the microwave equipment does not interfere with other electronic equipment. Industrial standards may be related to patient safety, such as, for example, providing sufficient electrical isolation between a generator and a patient. As such, the microwave energy generation and transmission devices are specifically designed to minimize and reduce undesirable energy delivery.

One common design practice used to ensure patient safety in electrosurgical generators is to create an isolation barrier between the generator and the patient. This is accomplished by isolating the generator output from an earth ground. Isolation barriers may be created by various generally accepted circuits, such as, for example, a transformer or capacitors that would have a low impedance at about 60 Hz. While the practice of including an isolation barrier is generally effective with systems delivering energy in RF frequencies, delivering energy with a signal in a microwave frequency provides new opportunities for microwave generator and system designers.

One such opportunity for microwave generators and their system designers is that microwave generators need to pass FCC regulations for EMC while operating. The fundamental frequency (i.e., the frequency band of the desirable microwave signal) is usually in an Instrumental Scientific Medical (ISM) band and is not an issue. Instead, EMC issues typically evolve around unintended energy discharges at frequencies outside of the IMS band, such as, for example, harmonics frequencies of the fundamental frequency above the ISM band.

Harmonics of the fundamental frequency may be a product of the microwave generator's signal generator or may be induced at various locations in the microwave generator circuits and/or the microwave energy delivery circuit. For example, harmonics are sometimes a product of the isolation barrier that is intended to isolate the generator from the patient and to provide patient safety. For example, the isolation barrier in a microwave delivery system may include the floating of the coaxial shield (i.e., the practice of not attaching the coaxial shield to the ground of the generator). Microwave energy may run along the shield of the coaxial cable and cause the coax cable to radiate as an antenna. This antenna affect can cause the generator's harmonics to be amplified and fail one or more EMC standards.

The present disclosure describes a system including an isolation apparatus to reduce undesirable EMC during the delivery of microwave energy.

SUMMARY

The present disclosure relates generally to a system and isolation apparatus for reducing undesirable radiated emissions during a medical procedure. More particularly, in one embodiment of the present disclosure a system includes a microwave generator that supplies microwave energy at a fundamental frequency, a coaxial transmission cable that transmits microwave energy between the microwave generator and a microwave energy delivery device and an isolation apparatus connected between the microwave generator and the coaxial transmission cable. The isolation apparatus is configured to electrically isolate the coaxial transmission cable from the microwave generator and capacitively couple the microwave generator ground to the coaxial transmission cable.

The isolation apparatus may further include an isolation circuit board configured to electrically isolate the microwave generator and the coaxial transmission cable while passing microwave energy therebetween. In one embodiment a ground reference shield may be connected to a microwave generator ground reference and configured to house the isolation circuit board. In another embodiment an isolation barrier may be positioned between the ground reference shield and the patient reference shield.

In yet another embodiment the ground reference shield and the patient reference shield may form a capacitor and capacitively couple the microwave generator ground reference to the coaxial transmission cable. The capacitive coupling between the ground reference shield and the patient reference shield may be adjustable. By varying the overlapping surface area between the ground reference shield and the patient reference shield, the gap between the overlapping portions of the ground reference shield and the patient reference shield or a dielectric property of the isolation barrier.

In still another embodiment according to the present disclosure, an isolation apparatus includes an isolation circuit board with an isolation circuit and a shield coupling that provides isolation between a microwave generator and a coaxial transmission cable. The isolation circuit capacitively couples a microwave generator and a coaxial transmission cable. The isolation circuit board passes energy at a fundamental frequency between the microwave generator and the coaxial transmission cable. The shield coupling includes a ground reference shield connected to a ground reference of the microwave generator and a patient reference shield connected to the outer sheath of the coaxial transmission cable. The shield coupling is configured to house the isolation circuit board. The ground reference shield and the patient reference shield are capacitively coupled and form a shield coupling capacitor. The shield coupling capacitor provides a ground reference for the coaxial transmission cable.

In yet another embodiment, the isolation apparatus may include an isolation barrier between the ground reference shield and the patient reference shield. The capacitive coupling between the ground reference shield and the patient reference shield may be adjustable by varying the overlapping surface area between the ground reference shield and the patient reference shield, the gap between the overlapping portions of the ground reference shield and the patient reference shield, or a dielectric property of the isolation barrier.

DETAILED DESCRIPTION

Detailed embodiments of the present disclosure are described herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
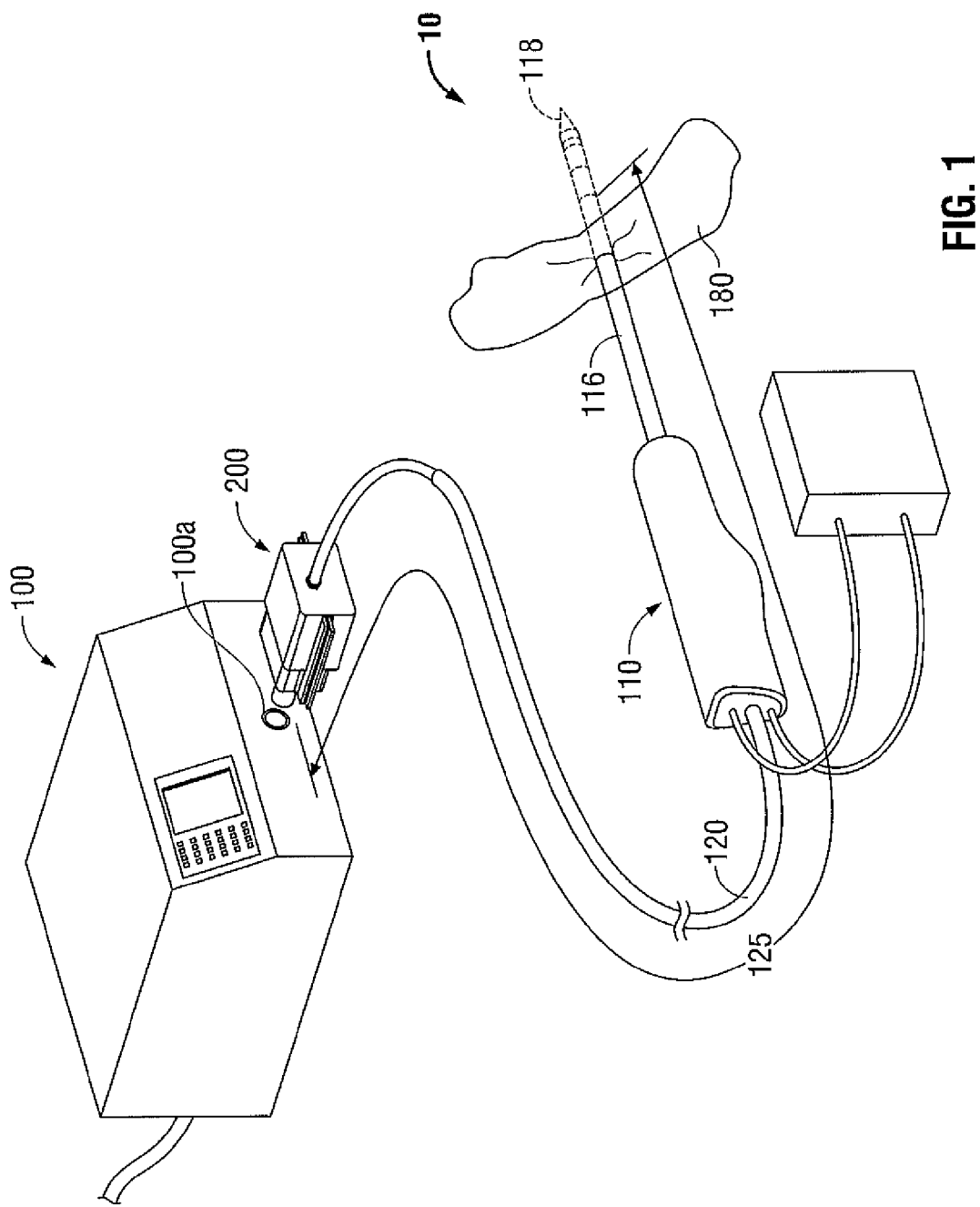
FIG. 1 is a functional block diagram of a microwave energy delivery including an isolation apparatus according to an embodiment of the present disclosure.

Referring to FIG. 1, a microwave energy delivery system including a microwave generator 100, a microwave energy delivery device 110, a coaxial transmission cable 120 and an isolation apparatus 200 employing embodiments of the present disclosure, is referenced generally as microwave delivery system as 10. The isolation apparatus 200 is connected between the microwave generator 100 and the microwave energy delivery device 110. In one embodiment of the present disclosure the isolation apparatus 200 connects to the coaxial connector 100a of the microwave generator 100 and the coaxial transmission cable 120. Isolation apparatus 200 may also be placed at various other positions in the microwave energy transmission circuit.

Microwave energy delivery device 110 includes coaxial transmission cable 120 (i.e., a coaxial transmission cable portion 120 is permanently affixed to the microwave energy delivery device 110), as illustrated in FIG. 1. Alternatively, coaxial transmission cable 120 may be separate from the microwave energy delivery device 110 and the isolation apparatus 200. In yet another embodiment, isolation apparatus 200 may include a coaxial transmission cable portion (not shown).

In yet another embodiment, the microwave energy transmission path 125 includes the transmission path of the isolation apparatus 200, the coaxial transmission cable 120 and the handle 116 (the transmission portion of the microwave energy delivery apparatus 110 proximal the antenna 118). The length of the microwave energy transmission path 125 is related to at least one parameter of the fundamental frequency of the energy generated by the microwave generator 100.

As illustrated in FIG. 1, microwave energy delivery device includes a percutaneous device having a sharpened tip configured to penetrate tissue. Isolation apparatus 200 may also be used with a catheter insertable microwave energy delivery device, a skin surface treatment microwave energy delivery device and a deployable microwave energy delivery device or other suitable device configured to delivery microwave energy to tissue 180.

Figure 2A:
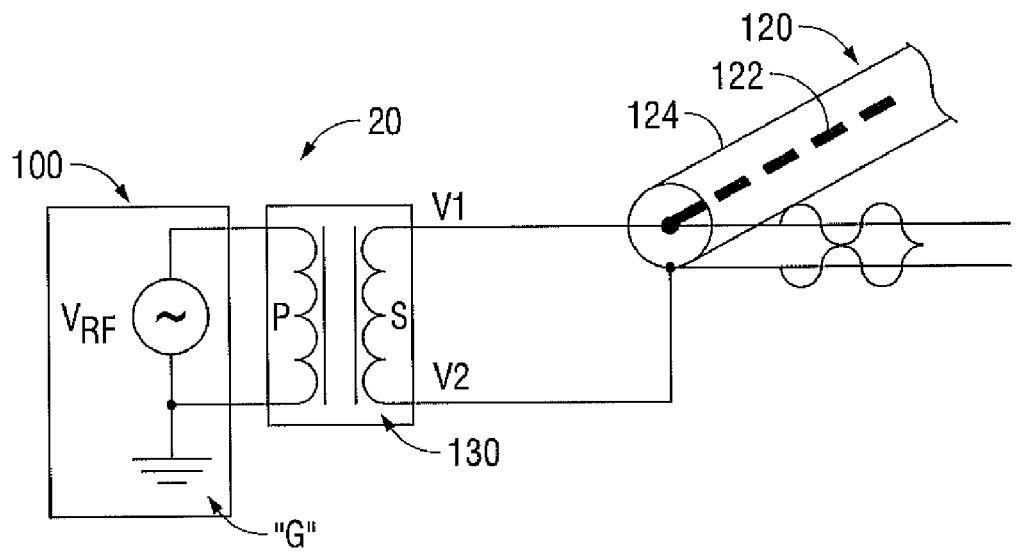
FIG. 2A is an electrical schematic of a conventional microwave energy delivery circuit.

FIG. 2A is an electrical schematic of a conventional microwave energy delivery circuit 20 without an isolation apparatus of the present disclosure. The circuit 20 includes a microwave energy source "VRF", a generator isolation device 130 (i.e., a transformer), and an electrical load 120 (i.e., a coaxial transmission cable 120 connected to a microwave energy delivery device (not shown)). In FIG. 2A, and as described herein, transformer 130 is shown merely as an example of a suitable generator isolation device. Generator isolation device 130 may be any suitable device that transfers energy from a first electrical circuit (microwave energy source VRF) to a second electrical circuit (electrical load 120) without direct electrical contact, such as, for example, by inductive coupling, capacitive coupling or antenna to antenna energy transfer (wireless).

Figure 2B:
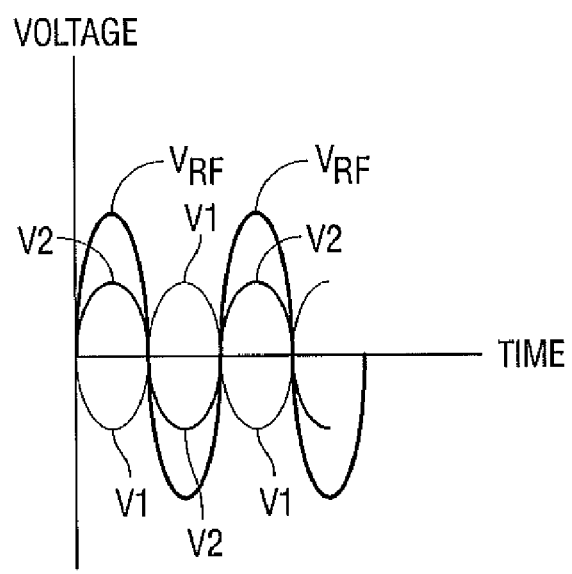
FIG. 2B is a plot of electrical waveforms, from a conventional microwave energy delivery circuit, at various points of the simplified electrical schematic of FIG. 2A.

FIG. 2B is a plot of electrical waveforms at various points in the simplified electrical schematic of FIG. 2A. The microwave generator generates the signal VRF that is applied to the primary side "P" of the generator isolation device 130 with general characteristics of a peak-to-peak amplitude, a phase and a fundamental frequency. VRF is referenced to ground "G" and is transformed across the generator isolation device 130 to the secondary side "S" of the generator isolation device 130 thereby creating a signal at "V1" and "V2" of the second electrical circuit. V1 and V2 have the same fundamental frequency of VRF and related by the formula:

$$VRF = (V1 - V2)/ID_{Eff}$$

wherein the constant "ID"$_{Eff}$ accounts for system losses in the circuit 20. The peak-to-peak amplitude of each of V1 and V2 is about half the peak-to-peak amplitude of VRF.

An ungrounded coaxial transmission cable 130 attached to the secondary S of the isolation device 130 carries half of the voltage on the inner conductor 122 and half of the voltage on the outer sheath 124, as illustrated in FIGS. 2A and 2B. This voltage signal V2 applied to the outer sheath 124 may cause energy to radiate from the coaxial transmission cable 120 thereby producing unwanted and excess radiation. In addition, carrying this signal V2 on the outer sheath 124 may result in the generation of standing waves and the generation of unwanted harmonics of the fundamental frequency. As such, the microwave generator 100, the transmission path 125 or the microwave energy delivery device 110 of FIG. 1 may fail radiating limits set by the FCC and may also result in undesirable heating of material or tissue in contact with the outer sheath 124.

Figure 3A:
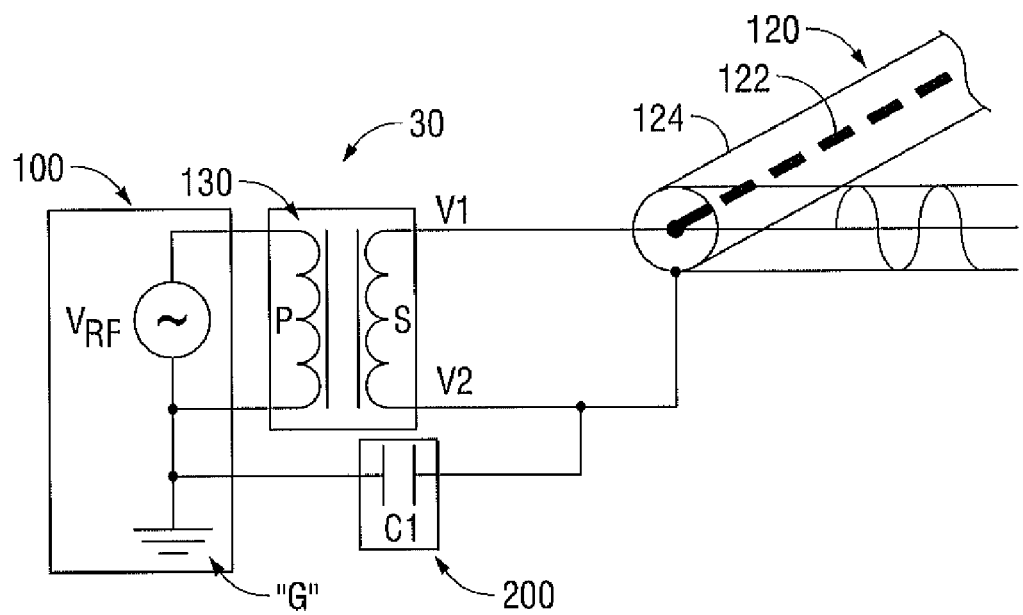
FIG. 3A is a simplified electrical schematic of a microwave energy delivery circuit including an isolation apparatus of the present disclosure.

FIG. 3A is an electrical schematic of a microwave energy delivery circuit 30 with an isolation apparatus 200 according to one embodiment of the present disclosure. The circuit includes a microwave energy source VRF, a generator isolation device 130 (i.e., a transformer), and an electrical load 120 (i.e., a coaxial transmission cable 120 connected to a microwave energy delivery device (not shown)) and an isolation apparatus 200. Isolation apparatus 200 includes a circuit exhibiting the properties of the present disclosure as described herewithin and is illustrated in the schematic as "C1". The capacitance values and properties of the circuit C1 in the isolation apparatus 200 is sufficiently sized such that the circuit C1 has a low impedance at the fundamental frequency of the microwave generator 100 and a high impedance at low frequencies.

Figure 3B:
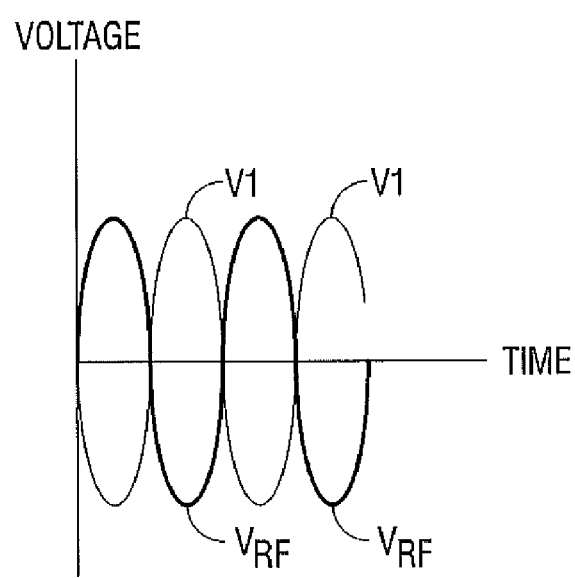
FIG. 3B is a plot of electrical waveforms at various points of the simplified electrical schematic of FIG. 3A.

With the isolation apparatus 200 in the circuit 30, the secondary side S at V2 at the fundamental frequency is capacitive coupled to ground G. FIG. 3B is a plot of the electrical waveforms at VRF and V1. V2 is at ground potential G and is therefore not illustrated in FIG. 3B. V1 is 180° out of phase relative to VRF and the magnitude is related by the formula:

$$VRF=V1/ID_{Eff}$$

wherein the constant "ID"$_{Eff}$ accounts for system losses in the circuit 30. As such, the peak-to-peak amplitude of each of V1 is approximately equal to the peak-to-peak amplitude of VRF and the majority of the microwave signal is carried on the inner conductor 122 of the coaxial transmission cable 120.

The isolation apparatus 200 provides an AC reference point to ground potential for the coaxial outer sheath 124 thus reducing the radiated signal of the coaxial transmission cable. V2 is capacitively coupled to ground potential G and the voltage at V2 is substantially zero.

Figure 4:
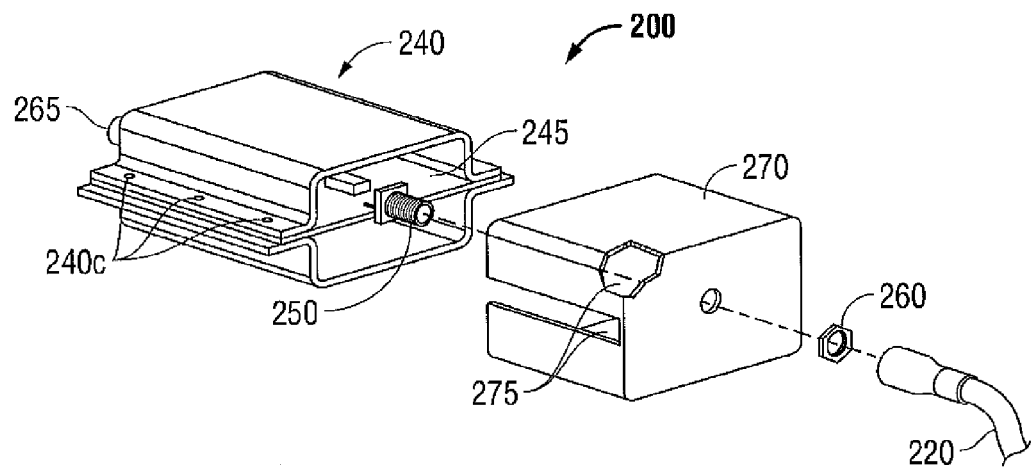
FIG. 4 is a perspective view of an isolation apparatus according to an embodiment of the present disclosure.
Figure 5:
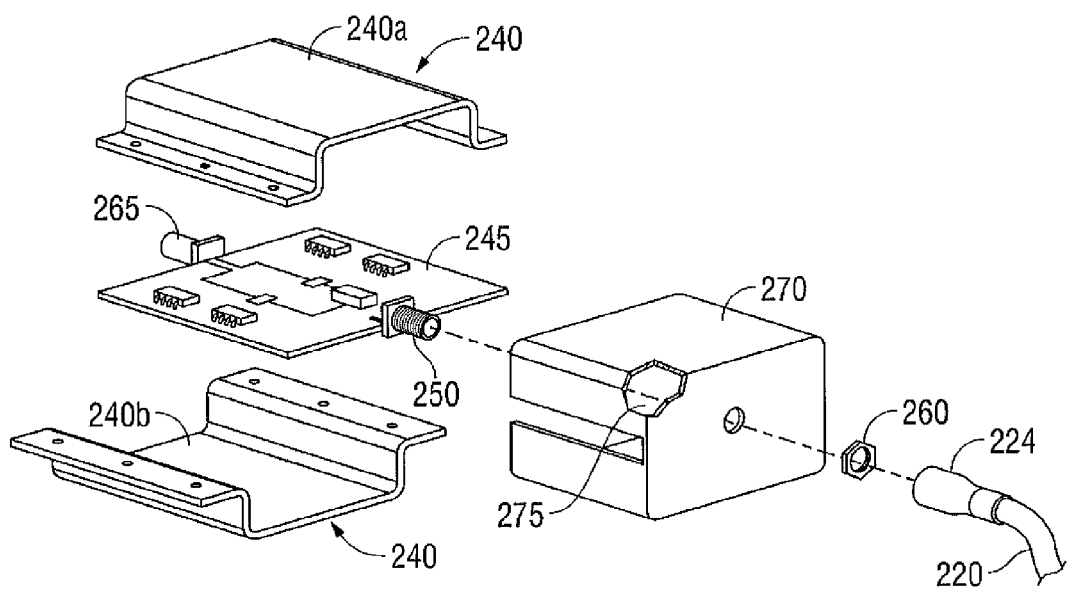
FIG. 5 is an exploded view of the isolation apparatus of FIG. 4.

FIGS. 4 and 5 are perspective views of an isolation apparatus 200 according to an embodiment of the present disclosure. Isolation apparatus 200 includes a ground reference shield 240, an isolation apparatus circuit board 245, a shield connector 250, a generator side connector 265 and a patient reference shield 270.

Ground reference shield 240 may include an upper shield 240a and a lower shield 240b connected at one or more positions. Upper and lower shields 240a, 240b may be formed of a suitable conductive material capable of forming a capacitive relationship with the patient reference shield 270. The capacitive relationship between the ground reference shield 240 and the patient reference shield 270 is described in more detail hereinbelow.

Upper and lower shields 240a, 240b may be connected by one or more mechanical connectors 240c, such as, for example, pins, rivets, fasteners, screws or bolts, or by a suitable connection, such as, for example, a compression connection a hinge connection, a welded or press fit connection. Alternatively, upper and lower shields 240a, 240b may have a combination of connection means, such as, for example, a hinge connection on a side and a locking mechanism or connector on a second side. Any suitable assembly may be used provided the ground reference shield 240 and the patient reference shield 270 form a desirable capacitive relationship therebetween.

Upper and lower shields 240a, 240b are in electrical communication with each other. As illustrated in FIG. 4, mechanical connection 240c may provide a suitable electrical connection between the upper and lower shields 240a, 240b. In another embodiment, upper and lower shields 240a, 240b may be electrically connected via the generator side connector 265.

Patient reference shield 270 is connected to the shield connector 250 by a suitable connector, such as, for example, a threaded shield connector attachment nut 260. Any other suitable connection may be used, such as, for example, a press-fit connection, a slot-fit connection, a locking connection or a welded connection.

Patient reference shield 270, shield connector 250 and the outer sheath 224 of the coaxial transmission cable 220 are in electrical communication with each other. Attachment nut 260 may provide a suitable connection between the patient reference shield 270 and the shield connector 250. Outer sheath 224 of the coaxial transmission cable 220 may connect to the shield connector 250 by a suitable connection, such as, for example, a threaded connection or a press-slip connection. Any other suitable connection may be used provided that it provides suitable electrical contact between the shield connector 250, the patient reference shield 270 and the outer sheath 224.

Patient reference shield 270 is configured to at least partially surround at least a portion of the ground reference shield 240 forming a capacitance gap there between. Gap may be controlled by the thickness of an isolation barrier 275 positioned between the patient reference shield 270 and the ground reference shield 240.

Isolation barrier 275 may be configured as a layer (or laminate) placed adjacent to or formed on one or more surfaces of the patient reference shield 270 and/or the ground reference shield 240. For example, the isolation barrier 275 may be a dielectric paper, such as a dielectric paper sold by DuPont under the trademark NOMEX®. Dielectric paper may be applied to or positioned adjacent the inner surface of the patient reference shield 270 prior to or during assembly. After assembly, the dielectric paper provides a minimum separation or spacing between the inner surface of the patient reference shield 270 and the outer surface of the ground reference shield 240.

Isolation barrier 275 may be a laminate such as, for example an organic-ceramic laminate sold by TACONIC under the product line of RF-35 High Performance Laminates. RF-35 provides suitable peel strength, low moisture absorption and a low dissipation factor thereby minimizing phase shift with frequency. RF-35 may include woven fabric and ceramics and may be coated on one or more surfaces of the isolation apparatus.

In yet another embodiment the isolation barrier 275 may be air. A separation distance between the inner surface of the patient reference shield 270 and the outer surface of the ground reference shield 240 may be maintained by a plurality of insulating offsets (not shown) that provide a desirable separation distance.

The various properties of the isolation apparatus 200 depend on the conductive relationship between the patient reference shield 270 and the ground reference shield 240. The patient reference shield 270 and the ground reference shield 240, separated by a minimal separation distance, form a parallel plate capacitor wherein the capacitance is proportional to the area of opposing shield 240, 270 surfaces and the permeability of the isolation barrier 275 and inversely proportional to the distance between the shields 240, 270.

The capacitance of a parallel-plate capacitor is equal to:

$$\text{Capacitance}=(\in \times A)/d$$

wherein "∈" is the permittivity of the isolation barrier 275, "A" is the area of the opposing shields 240, 270 and "d" is the spacing between the shields 240, 270.

As such, a desired capacitance may be obtained by varying one or more of the area of overlapping surfaces, the dielectric properties of the isolation barrier 275, and the gap between the two opposing shields 240, 270.

In yet another embodiment of the present disclosure the capacitance of the isolation apparatus 200 may be adjustable. In one embodiment, a gap adjustment mechanism (not shown) may vary the position of the ground reference shield 240 relative to the patient reference shield 270 thereby increasing or decreasing the gap therebetween. Gap adjustment mechanism (not shown) may change the gap dynamically or manually. A dynamic adjustment may be necessary if the microwave generator varies the fundamental frequency during energy delivery. A manual adjustment may be used to calibrate the isolation apparatus 200 during assembly.

Capacitance of the isolation apparatus 200 may be adjusted by varying the overlap between the ground reference shield 240 and the patient reference shield 270. Overlap adjustment mechanism (not shown) may reposition the shields 240, 270 relative to each other either dynamically or manually.

Capacitance of the isolation apparatus 200 may be adjusted by changing the dielectric properties of the isolation barrier 275 or by changing the type of material used for the isolation barrier.

Isolation circuit board 245 is housed within the ground reference shield 240 of the isolation apparatus 200. Isolation circuit board 245 may include a circuit configured to provide isolation between a microwave generator (not shown) and a coaxial transmission cable 220, as discussed hereinabove.

Figure 6:
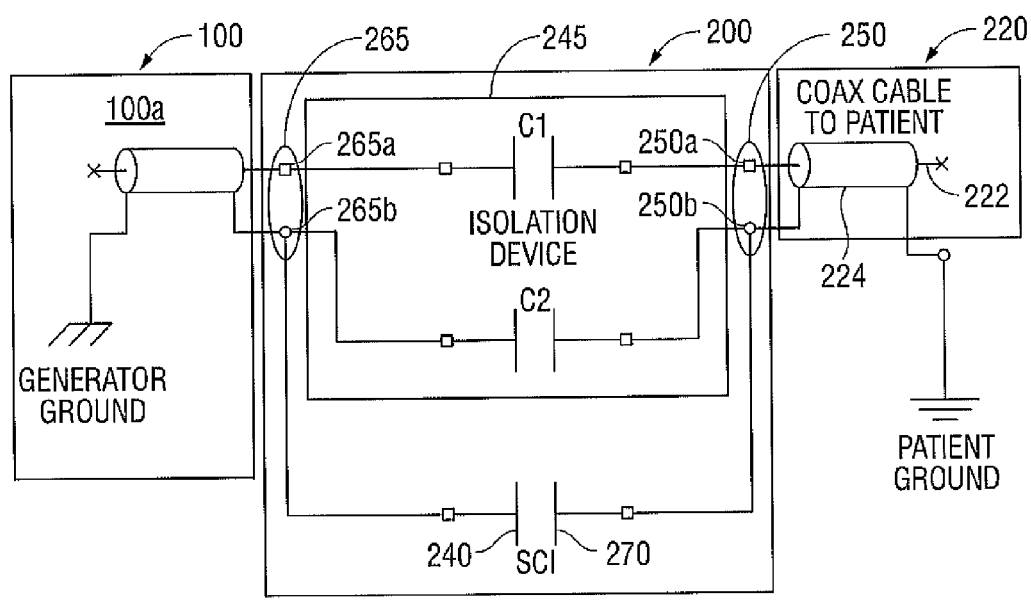
FIG. 6 is an electrical schematic of the isolation apparatus of FIG. 4 in a microwave energy delivery circuit.

FIG. 6 is an electrical schematic of the isolation apparatus of FIG. 4 and the microwave energy delivery system of FIG. 1. The adjacent surfaces of the ground reference shield 240, connected to the generator side connector 265, and the patient reference shield 270, connected to the coaxial sheath 224, form the shield coupling capacitor "SC1". Isolation circuit board 245 includes first and second isolation capacitors "C1" and "C2", respectively, that provide electrical isolation, as discussed herein above, between the microwave generator 100 and the coaxial transmission cable 220.

In use, a microwave signal is supplied to the generator side connector 265. The inner conductor 265a of the microwave generator connector 265 connects to the first isolation capacitor C1. The outer conductor 265b of the microwave generator connector 265 connects to the second isolation capacitor C2 and to the ground reference shield 240 of the shield coupling capacitor SC1. At the fundamental frequency of the microwave energy delivery system the first and second isolation capacitor C1, C2 appear as short circuits and pass the signal at the fundamental frequency to the inner conductor 250a and the outer conductor 250b, respectively, of the shield connector 250 and to the inner conductor 222 and the outer sheath 224 of the coaxial transmission cable 220. The patient reference shield 270, connected to the outer sheath 224 of the coaxial transmission cable, and the ground reference shield 240 form the shield coupling capacitor SC1 thereby providing a ground reference for the coaxial transmission cable 220.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A system for reducing radiated emissions, the system comprising:
    a microwave generator that supplies microwave energy at a fundamental frequency;
    a coaxial transmission cable that transmits microwave energy between the microwave generator and a microwave energy delivery device; and
    an isolation apparatus connected between the microwave generator and the coaxial transmission cable, the isolation apparatus configured to electrically isolate the coaxial transmission cable from the microwave generator,
    wherein capacitance of the isolation apparatus is selectably adjustable.

2. The system according to claim 1, wherein the isolation apparatus further includes:
    an isolation circuit board configured to electrically isolate the microwave generator and the coaxial transmission cable while passing microwave energy therebetween.

3. The system according to claim 2, wherein the isolation apparatus further includes:
    a ground reference shield connected to a microwave generator ground reference and configured to house the isolation circuit board;
    a patient reference shield at least partially surrounding the ground reference shield and forming a capacitive relationship therebetween, and
    wherein the ground reference shield and the patient reference shield are configured to form a capacitor and to capacitively couple the microwave generator ground reference to the coaxial transmission cable.

4. The system according to claim 3, wherein the isolation apparatus further includes: an isolation barrier between the ground reference shield and the patient reference shield.

5. The system according to claim 3, wherein the capacitive coupling between the ground reference shield and the patient reference shield is dynamically adjustable.

6. The system according to claim 3, wherein the capacitance of the capacitor formed between the ground reference shield and the patient reference is selectively adjusted by varying the gap between the overlapping portions of the ground reference shield and the patient reference shield.

7. The system according to claim 3, wherein the capacitance of the capacitor formed between the ground reference shield and the patient reference shield is manually adjustable.

8. The system according to claim 1, wherein the capacitance of the capacitor formed between the ground reference shield and the patient reference is selectively adjusted by varying the overlapping surface area between the ground reference shield and the patient reference shield.

9. The system according to claim 4, wherein the capacitance of the capacitor formed between the ground reference shield and the patient reference shield is selectively adjusted by varying a dielectric property of the isolation barrier.

* * * * *